United States Patent [19]

Bernadat

[11] Patent Number: 5,074,792
[45] Date of Patent: Dec. 24, 1991

[54] PROSTHESIS FOR DEVITALIZED TOOTH

[76] Inventor: Georges Bernadat, Le Clos du Renoillet rue du Mazet Communay, 69360 Saint Symphorien D'Ozon, France

[21] Appl. No.: 487,713
[22] Filed: Mar. 2, 1990

[30] Foreign Application Priority Data

Mar. 2, 1989 [FR] France ............... 89 03001

[51] Int. Cl.⁵ ............... A61C 5/08
[52] U.S. Cl. ............... 433/220; 433/224
[58] Field of Search ............... 433/220, 221, 224

[56] References Cited

U.S. PATENT DOCUMENTS 4,253,835  3/1981  Ware ............... 433/220
4,622,012  11/1986  Smoler ............... 433/221
4,952,150  8/1990  Schiwiora et al. ............... 433/220

FOREIGN PATENT DOCUMENTS 959312   12/1974  Canada ............... 433/220
0299919  1/1989   European Pat. Off. .
2588181  4/1987   France .

OTHER PUBLICATIONS

Search Report issued in priority application (French 89 03 001) listing the two patents being filed herewith.

Primary Examiner—Robert P. Swiatek
Assistant Examiner—Nicholas D. Lucchesi
Attorney, Agent, or Firm—Herbert Dubno; Andrew M. Wilford

[57] ABSTRACT

A devitalized tooth having an outer surface at which opens a longitudinally extending and empty pulp cavity into which open transverse tubules is rebuilt by a prosthesis comprising a peg engaged with spacing in the cavity and having an outer end projecting from the cavity past the outer surface of the tooth, a prosthesis body adhered to the outer end of the peg, and a generally conical flexible and porous sheath formed of high-strength filaments surrounding the peg in the cavity. A solid mass formed of a durable resin that has a very low surface tension when liquid fills the cavity around the peg and the tubules. The sheath is wholly imbedded in the cavity in the mass.

14 Claims, 4 Drawing Sheets

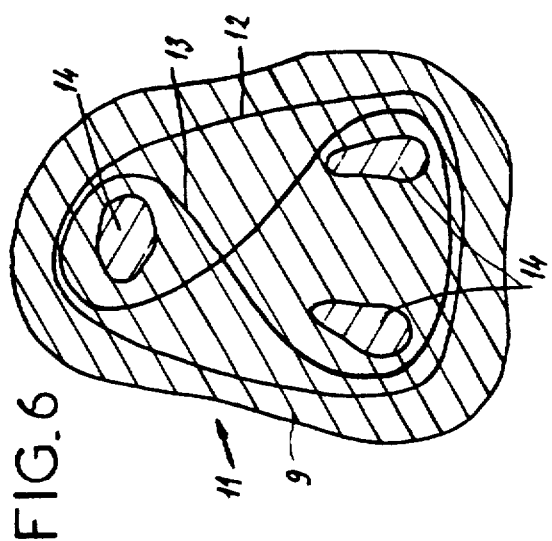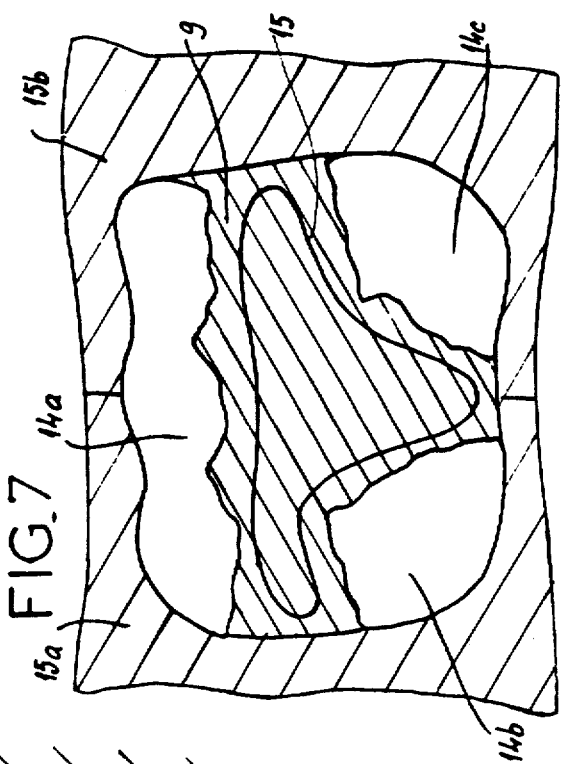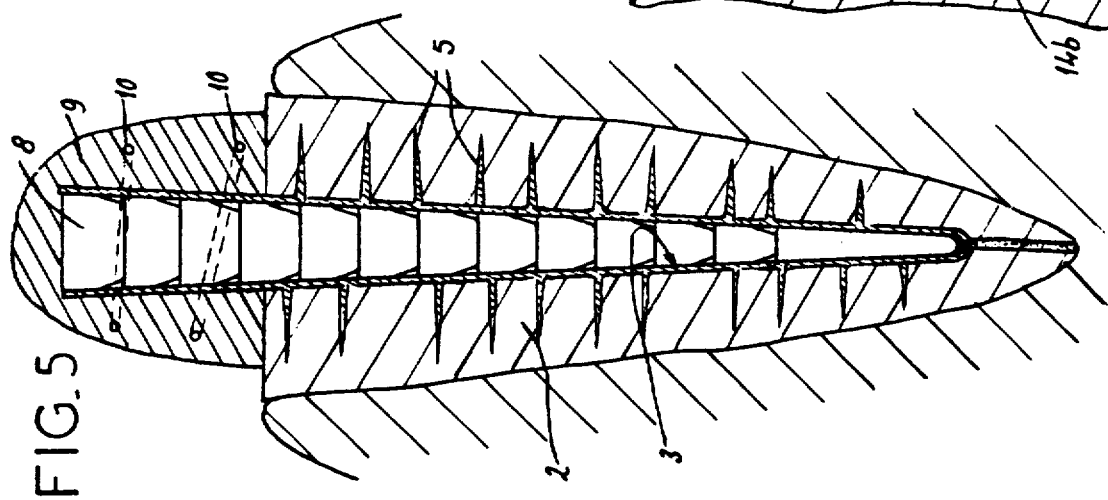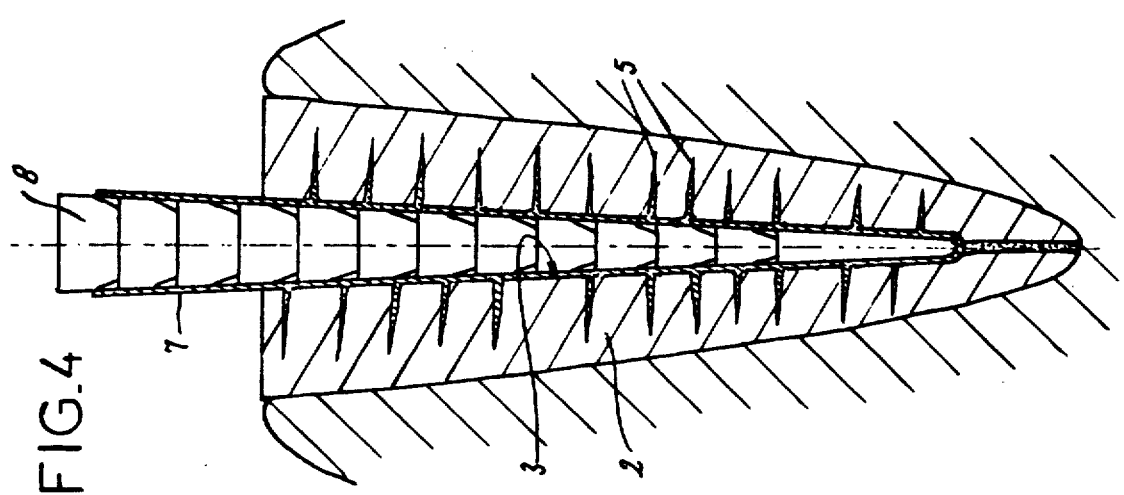

PROSTHESIS FOR DEVITALIZED TOOTH

FIELD OF THE INVENTION

The present invention relates to a dental prosthesis. More particularly this invention concerns a prosthesis for a devitalized tooth, that is a tooth whose root canal and pulp cavity have been cleaned of pulp, and a method of making such a prosthesis.

BACKGROUND OF THE INVENTION

When a tooth is devitalized it loses part of its elasticity and strength. The tooth becomes more fragile because it loses its live protein core and because it also becomes an anchor for a stem of a prosthesis. Often lateral forces on a crown or cap mounted on a peg seated in the bored-out tooth are mainly effective at an interface lying at an outer surface of the tooth. The bond at this interface eventually opens, allowing foreign matter to get into the tooth and causing localized action frequently breaking the peg or tenon off the prosthesis. Even if only one of several such anchors breaks, the entire prosthesis must be removed to do the necessary repair.

In a standard procedure a small screw is cemented into the bored-out tooth root. A ring is mounted on this screw and the cap or crown is built up on the ring.

It is also known to bore out the tooth to form therein a cavity whose shape corresponds to that of a tapered plug that is subsequently fitted to it. This arrangement often requires removal of vital strength-imparting dentin so that, even though the plug is very well seated, the tooth is in effect weakened by the installation.

All of the known procedures have in common that they add nothing to the strength of the tooth. In fact many known systems actually weaken the already reduced strength of the devitalized tooth.

OBJECTS OF THE INVENTION

It is therefore an object of the present invention to provide an improved dental prosthesis for a devitalized tooth.

Another object is the provision of such an improved dental prosthesis for a devitalized tooth which overcomes the above-given disadvantages, that is which actually increases the strength of such a tooth.

A further object is to provide an improved method of making such a prosthesis.

SUMMARY OF THE INVENTION

A devitalized tooth having an outer surface at which opens a longitudinally extending and empty pulp cavity into which open transverse tubules are rebuilt according to the invention by a prosthesis comprising a peg engaged with spacing in the cavity and having an outer end projecting from the cavity past the outer surface of the tooth, a prosthesis body adhered to the outer end of the peg, and a generally conical flexible and porous sheath formed of high-strength filaments surrounding the peg in the cavity. A solid mass formed of a durable resin that has a very low surface tension, when liquid, fills the cavity around the peg and the tubules. The sheath is wholly imbedded in the cavity in the mass.

Thus according to this invention the strong fibers forming the sheath actually reinforce the tooth. According to another feature of this invention the sheath is a porous knitted or woven textile and the filaments of the sheath form a tail imbedded in the mass. With the system of this invention the pulp cavity need not be made into a predetermined shape, as the sheath will accommodate itself to any shape of pulp cavity, and the resin will be able to soak into any hollow part of the tooth, which is thoroughly cleaned out. The tail of the sheath forms a reinforcement at the critical interface of the prosthesis body and the tooth outer surface and the resin mass extends virtually to the hyaline layer.

In accordance with further features of this invention a reinforcing ring is imbedded in the body around the outer end of the peg. In addition the resin is of the type which hardens in the absence of air. Such a resin does not expand as it hardens so as to avoid breaking the tooth and also does not contract, so that it completely fills any voids in the tooth.

Furthermore the peg is formed by a plurality of like but separate tapered rods generally filling the sheath, the rods forming interstices filled by the mass. The rods taper at an apex angle of from 0.5° to 1.5°. These rods can be of circular, oval, or polygonal section. In any case they fit snugly together to completely fill even an irregularly shaped pulp cavity. This eliminates the need to machine the pulp cavity to a predetermined shape, thereby weakening the tooth.

The filaments according to this invention are an aromatic polyamide, for instance the high-strength resin sold as Kevlar ®. The resin itself can be methyl dimethacrylate.

The method of this invention comprises the steps of first lining the cavity of the devitalized tooth with a generally conical flexible and porous sheath formed of high-strength filaments, then fitting in the lined cavity a peg so that an outer end of the peg projects from the cavity past the outer surface of the tooth, and finally filling the tubules and the cavity around the peg with a hardenable liquid resin of low surface tension so as to completely imbed the sheath in the cavity in the resin. This resin is hardened into a solid mass in which the sheath is imbedded in the cavity in the mass and a prosthesis body is then formed that is adhered to the outer end of the peg.

DESCRIPTION OF THE DRAWING

The above and other objects, features, and advantages will become more readily apparent from the following, reference being made to the accompanying drawing in which:

FIGS. 4 and 5 are longitudinal sections through the tooth in third and fourth steps of the method of this invention;

FIGS. 6 and 7 are horizontal sections through crowns made according to the present invention;

SPECIFIC DESCRIPTION

Figure 1:
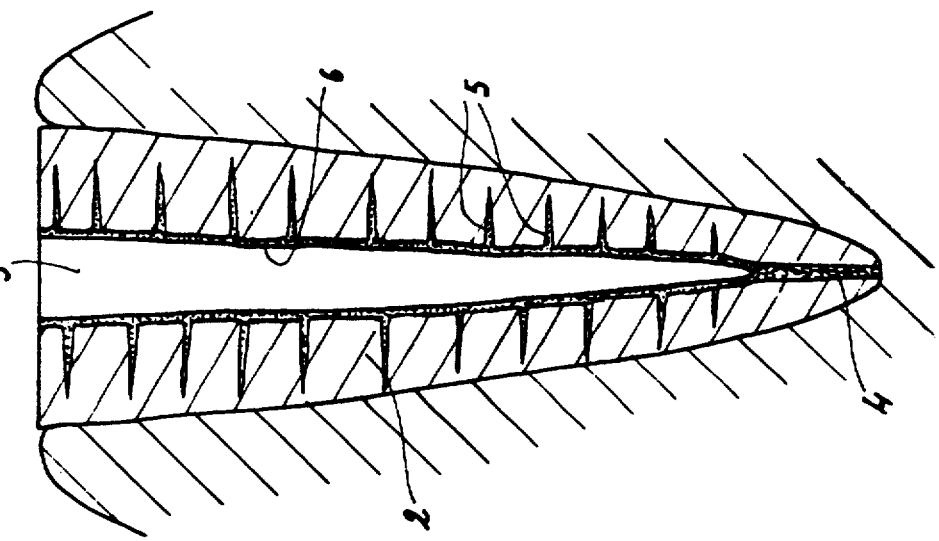
FIGS. 1 and 2 are longitudinal sections through a devitalized tooth according to the first two steps of the method of this invention.

As seen in FIG. 1 a devitalized tooth root 2 seated in gum tissue 1 has a pulp canal 3 and a root canal 4. The canals 3 and 4 and radial tubules 5 of the tooth 2 have been thoroughly cleaned out, for instance by mechanical action and flushing with very concentrated soda solution, then the root canal 4 is plugged with an elastomeric plug 18, for instance of gamboge. The tooth is then dried, flushed with alcohol or the like, and redried.

A liquefied resin of the type that can harden in the absence of air without expansion or contraction is then introduces into the cavity 3 to form in same a resin lining 6 and to fill the tubules 5. Methyl dimethylacrylate can be used as the resin. Once hardened, with the resin extending virtually to the hyaline layer in the tubules 5, the tooth 2 is substantially strengthened.

Figure 2:
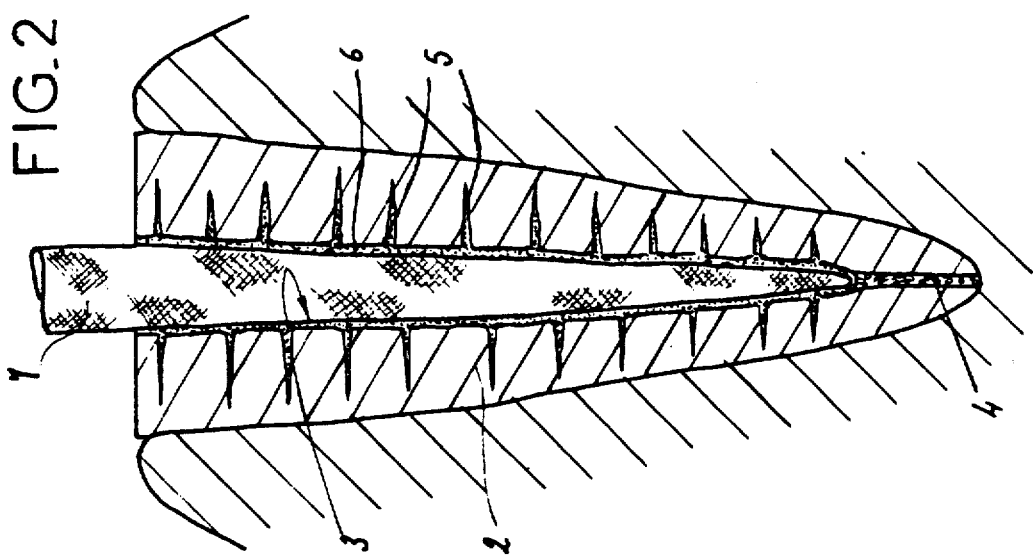
Figure 3:
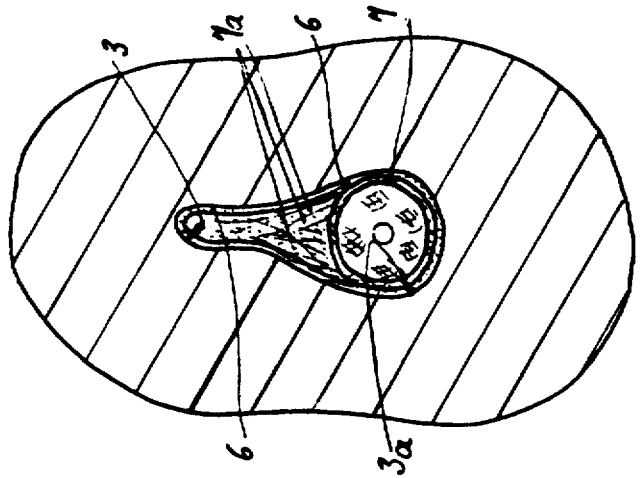
FIG. 3 is a top view of the tooth as seen in FIG. 2.

Then as shown in FIGS. 2 and 3 a conical sheath 7 of a porous Kevlar ® fabric is fitted into the lined cavity with a tail 7a of this sheath lying to the side in a lateral extension of the cavity. Subsequently as seen in FIG. 4 a ridged peg 8 is inserted into the sheath 7 so that both the sheath 7 and peg 8 extend somewhat past the outer surface of the tooth 2, at the gum line. The peg 8 is formed with sawtooth ridges directed to resist withdrawal of itself from the tooth 2. To accommodate the peg 8, the cavity 3 can be machined out complementarily at 3a.

Finally as seen in FIG. 5 a mass 9 which can be of the same resin as the resin 6 is cast around the top of the peg 8, to which some reinforcing rings 10 have been fitted. This forms the basis for a crown which can thereafter be constituted in the manner known per se.

FIG. 6 shows a crown 11 having reinforcement rings 12 and 13 encircling fragments 14 of the teeth. In FIG. 7 three fragments 14a, 14b, and 14c are united by a ring 15. Mold parts 15a and 15b are used to make the structure.

Figure 8:
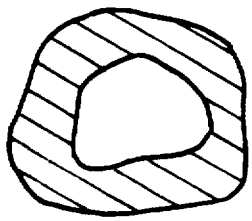
FIGS. 8 through 11 illustrate the shapes of various pulp cavities.
Figure 9:
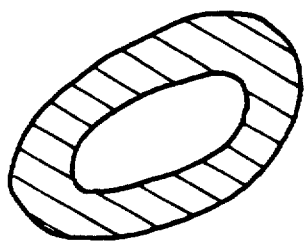
Figure 10:
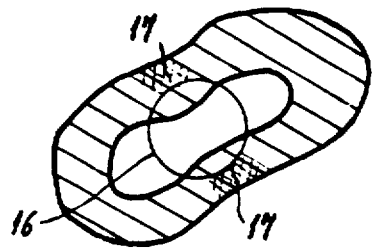
Figure 11:
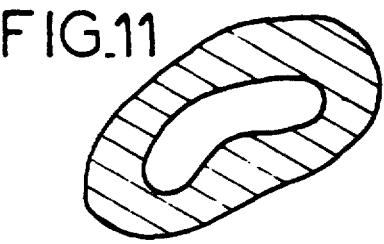

A pulp cavity can have a generally regular shape as seen in FIG. 8, an oblong shape such as shown in FIG. 9, or a highly irregular or C-shape as seen in FIGS. 10 and 11. Clearly if the dumbbell-section cavity of FIG. 10 is reamed out to a circular shape as indicated by circle 16, wall portions 17 of the tooth will be substantially weakened. The normal machining operation also blocks the inner ends of the tubules 5, making it impossible to fill them subsequently.

Figure 12:
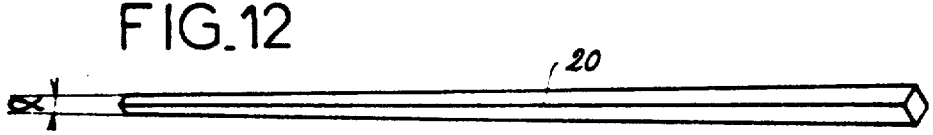
FIGS. 12 and 13 are side views of rods for forming pegs according to this invention.
Figure 13:
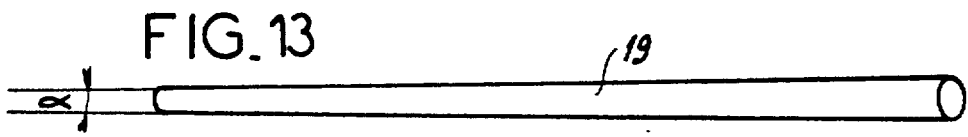
Figure 16:
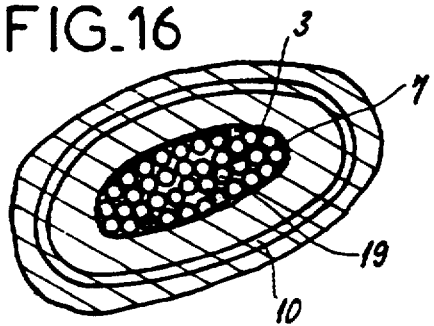
FIGS. 15 and 16 are cross sections through crowns formed respectively with the rods of FIGS. 12 and 13.
Figure 15:
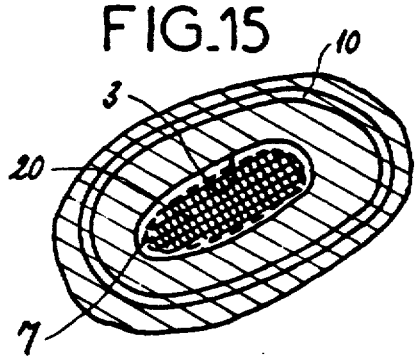
Figure 14:
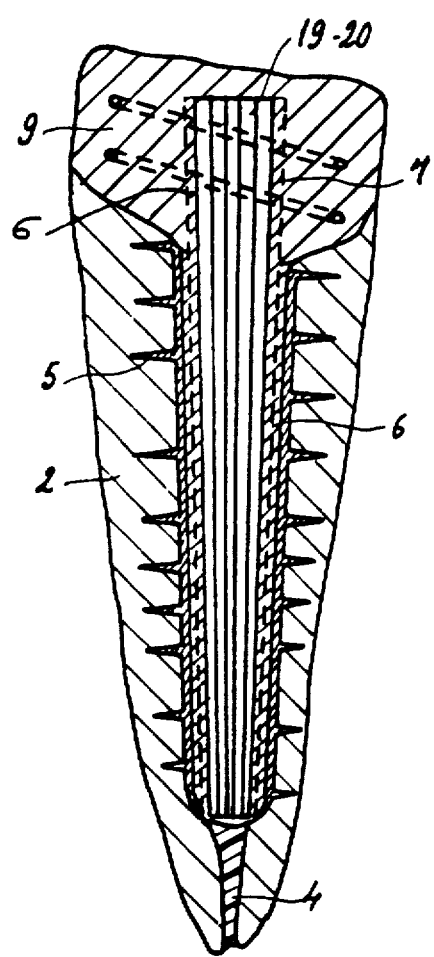
FIG. 14 is a longitudinal section through a tooth provided with a prosthesis using the rods of FIG. 13.

To this end the peg 8 according to this invention is made up of a bundle of rods. FIG. 12 shows a square-section rod 20 and FIG. 13 a round section rod 19. Both rods 19 and 20 taper at an angle α that lies between 0.5° and 1.5° and are between 20 mm and 25 mm long and between 0.2 mm and 0.7 mm across at their thickest ends. FIGS. 14 and 15 show how the square-section rods 20 fill a cavity 3 and FIG. 16 shows how the round rods 19 can fill an oblong cavity 3. In either case the interstices between the rods, which are made of a very strong plastic or metal, are filled with the resin 6 which bonds to them and unites them into an integral block filling the tooth 2. Thus a large number of these rods 19 or 20 must be used to fill a cavity 3.

Figure 17:
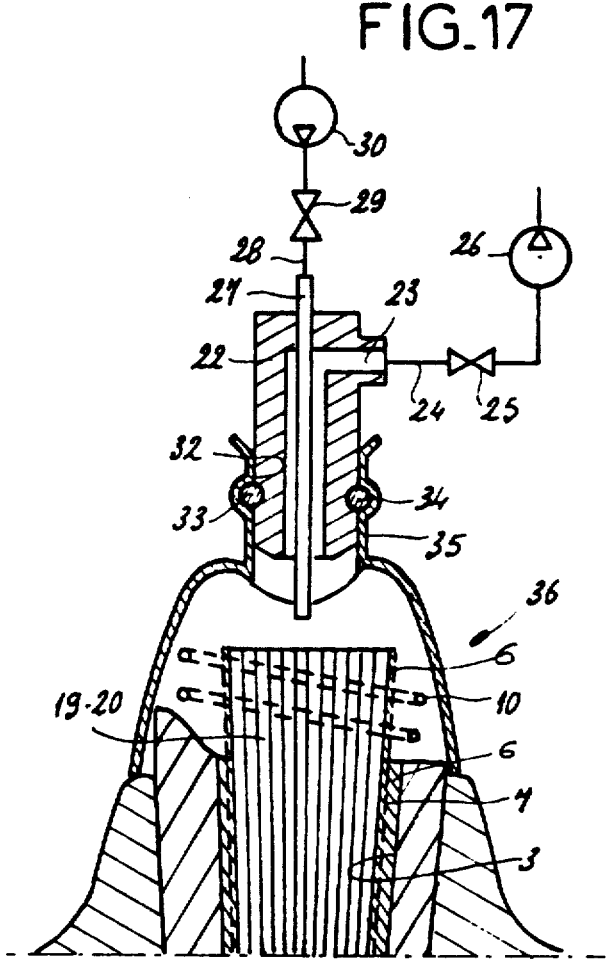
FIG. 17 is a largely diagrammatic longitudinal section through an apparatus for making a dental prosthesis according to the invention.

The resin 6 is cast about the tooth 2 after it is fitted with a lining 7 and rods 19 by an apparatus such as shown in FIG. 17. A fitting 22 is formed with a laterally open passage 23 connected via a line 24 and valve 25 to a vacuum pump 26 and has an axially throughgoing conduit 21 connected via a line 28 and valve 29 to a pump 30 that can supply the resin in liquefied form, under superatmospheric pressure. A flexible and thermoshapable skirt 36 has a lower edge 36a that is cut and shaped to fit snugly around the upper edge of the root 2 and a collar 35 that fits snugly around a neck 32 of the fitting 22, with a seal 34 provided between the two.

To start with the chamber inside the skirt 36 is evacuated by the pump 26 to a subatmospheric pressure. Then the valve 25 is closed and valve 29 is opened, and the resin 6 is pumped in. The subatmospheric pressure combined with the low surface tension of the resin 6 sucks this resin 6 into all the voids of the tooth 2, forming the above-described integral reinforcement.

The structure thus formed can be shaped into the desired form, or can serve as the base for anchoring a crown. The skirt 36 can be disposable.

I claim:

1. For use with a devitalized tooth having an outer surface at which opens a longitudinally extending and empty pulp cavity into which open transverse tubules, a prosthesis comprising:
    a peg engaged with spacing in the cavity and having an outer end projecting from the cavity past the outer surface of the tooth;
    a prosthesis body adhered to the outer end of the peg;
    a generally conical flexible and porous sheath formed of high-strength filaments surrounding the peg in the cavity; and
    a solid mass formed of a durable resin that has a very low surface tension when in liquid form filling the cavity around the peg and the tubules, the sheath being wholly imbedded in the cavity in the mass.

2. The dental prosthesis defined in claim 1 wherein the sheath is a porous textile.

3. The dental prosthesis defined in claim 2 wherein the filaments of the sheath form a tail imbedded in the mass.

4. The dental prosthesis defined in claim 1, further comprising
    a reinforcing ring imbedded in the body around the outer end of the peg.

5. The dental prosthesis defined in claim 1 wherein the resin is of the type which hardens in the absence of air.

6. The dental prosthesis defined in claim 1 wherein the peg is formed by a plurality of like but separate tapered rods generally filling the sheath, the rods forming interstices filled by the mass.

7. The dental prosthesis defined in claim 6 wherein the rods taper at an apex angle of from 0.5° to 1.5°.

8. The dental prosthesis defined in claim 6 wherein the rods have a polygonal cross-section.

9. The dental prosthesis defined in claim 1 wherein the filaments are formed of an aromatic polyamide.

10. The dental prosthesis defined in claim 1 wherein the resin is methyl dimethacrylate.

11. A method of making a prosthesis on a devitalized tooth having an outer surface at which opens a longitudinally extending and empty pulp cavity into which open transverse tubules, the method comprising the steps of:
    installing in the cavity a generally conical flexible and porous sheath formed of high-strength filaments;
    fitting in the sheath in the cavity a peg so that an outer end of the peg projects from the cavity past the outer surface of the tooth;

filling the tubules and the cavity around the peg with a hardenable liquid resin of low surface tension so as to completely imbed the sheath in the cavity in the resin;

hardening the resin into a solid mass in which the sheath is imbedded in the cavity in the mass; and forming a prosthesis body adhered to the outer end of the peg.

12. The method defined in claim 11 wherein the peg is fitted in the cavity by inserting in the cavity pointed ends of a multiplicity of generally identical tapered rods.

13. The method defined in claim 11, further comprising the step of fitting a ring around the outer peg end before forming the prosthesis body and imbedding the ring in the body.

14. The method defined in claim 11 wherein the tubules and cavity are filled with the resin in two stages as follows:

filling the tubules and lining the cavity with the hardenable liquid resin to form therein a resin lining prior to installing the porous sheath in the cavity; and filling the lined cavity around the sheath and peg with the resin after installing the sheath in the cavity and fitting the peg into the sheath.

* * * * *